United States Patent [19]

Philion et al.

[11] Patent Number: 5,659,083
[45] Date of Patent: Aug. 19, 1997

[54] PROCESS OF PREPARING 2,2'-(1-METHYL-1,2-ETHANEDIYLIDENE) BIS [HYDRAZINECARBOXIMIDAMIDE]

[75] Inventors: Richard Philion, Pottstown, Pa.; Martin Robert Gray, Alnwick, England

[73] Assignee: Sanofi, Paris, France

[21] Appl. No.: 655,512

[22] Filed: May 30, 1996

[51] Int. Cl.$^6$ ...................... C07C 281/18; A61K 31/155
[52] U.S. Cl. ............................................. 564/227; 514/632
[58] Field of Search ............................. 564/227; 514/632

[56] References Cited

U.S. PATENT DOCUMENTS 3,355,491  11/1967  Niles et al. ................................ 564/227
4,520,031  5/1985  Knight .................................... 514/632

OTHER PUBLICATIONS

Baiocchi et al, J. Med. Chem., 6, 431 (1963).
Oliverio et al, J. Pharm. Sci., 52, 202 (1963).

Primary Examiner—Peter O'Sullivan
Attorney, Agent, or Firm—Paul E. Dupont

[57] ABSTRACT

Process for the preparation of 2,2'-(1-methyl-1,2-ethanediylidine)bis[hydrazine carboximidamide] by
  a) removing impurities from aminoguanidine bicarbonate;
  b) reacting the aminoguanidine bicarbonate with methylglyoxal dimethyl acetal in an aqueous isopropyl medium; and
  c) purifying the 2,2'-(1-methyl-1,2-ethanediylidene)bis[hydrazine carboximidamide] by crystallization from an acidic aqueous-isopropanol medium.

5 Claims, No Drawings

PROCESS OF PREPARING 2,2'-(1-METHYL-1,2-ETHANEDIYLIDENE) BIS [HYDRAZINECARBOXIMIDAMIDE]

BACKGROUND OF THE INVENTION

1. Field of the Invention

The present invention relates to a process of preparing 2,2'-(1-methyl-1,2-ethanediylidene) bis[hydrazine carboximidamide] having greatly reduced impurities therein useful in a method of treating cancer or advanced malignant diseases.

2. Reported Developments

The compound 2,2'-(1-methyl-1,2-ethanediylidene)bis [hydrazine carboximidamide] is known by several names, such as 1,1'[(methylethanediylidene)dinitrilo] diguamidine, pyruvaldehyde bis (amidinohydrazone), mitoguazone and methylglyoxal bis-guanylhydrazone, methyl GAG or MGBG, represented by the formula

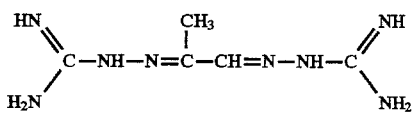

MGBG and its salts have been disclosed in the prior art since the 1950s for use against various diseases as illustrated by the following patents and publications.

The antitumor activity of MGBG in leukemia-L1210- and adenocarcinoma-755-bearing rodents was first reported by Freelander et al, 18 Cancer Res. 360 (1958).

Japanese 51044643 discloses MGBG and its acid addition salts as effective agents against virus diseases of fishes to prevent and treat infections, pancreatic necrosis and hematopoietic necrosis.

Japanese 50029520 discloses MGBG and its salts for use against influenza virus.

U.S. Pat. No. 4,201,788 discloses MGBG for the treatment of non-malignant proliferative skin diseases.

MGBG is known to inhibit S-adenosylmethionine decarboxylase (SAMD), which is a key enzyme in polyamine Synthesis, leading to cellular polyamine depletion. However, investigations with MGBG revealed unacceptable levels of toxicity. The toxicological effects of MGBG observed, some of which are peculiar to certain animal species, include gastrointestinal toxicity, delayed and fatal hypoglycemia, hepatic and renal damage, bone marrow depression, diarrhea and phlebitis. These effects have also prevailed in human subjects undergoing MGBG treatment. Additionally, several toxic effects were demonstrated which are unique to man. These include esophagitis, ulcerative pharyngitis, laryngitis, stomatitis, genital mucosa swelling, conjunctivitis, mucositis, erythema, edema, desquamating dermatitis, and profound anorexia with associated weight loss. Patients who were administered MGBG on a daily schedule exhibited remission to acute leukemia only after a precarious struggle with the oftentimes life threatening side effects. In many patients, treatment had to be discontinued before any beneficial results could be noted.

Knight et al in Can. Treat. Rep., 63 1933–1937 (1979) found that the levels of toxicity were dose schedule related and could be controlled. U.S. Pat. No. 4,520,031 addresses the issue of such does schedule related control in order to reduce toxicity.

The dose schedule control, as described in the patent was based on the postulation that MGBG exerts an inhibitory action relative to polyamine biosynthesis. Physiologically achievable effects of MGBG may be related to the inhibition of the enzyme S-adenosyl methionine decarboxylase, which catalyses the synthesis of the polyamine, spermidine.

Spermidine is believed to play an important role in the initiation of DNA synthesis. Studies have shown that MGBG-mediated depression of DNA synthesis is associated with spermidine depletion and putrescine accumulation.

Another area in which polyamines are believed to play a major role is in RNA synthesis, especially that of transfer (t) RNA. The methylation of tRNA may be directly stimulated by polyamines, a finding of particular interest in light of the reports that neoplastic tissue differs from normal tissue with respect to the extent of methylated tRNA. Here, too, spermidine appears to play a critical role.

Polyamine accumulation appears to be a necessary requisite to DNA synthesis at an optimal rate, in both normal and neoplastic tissues. Thus, the toxicity of MGBG observed in tissues with rapid turnover (skin, G.I. mucosa and bone marrow) may be directly related to inhibition of polyamine biosynthesis and a subsequent depletion of RNA and DNA, the agents which ultimately regulate cell replication. There is, however, strong evidence that: (1) polyamines are excreted in excess in the majority of cancer patients; (2) polyamines, especially spermidine, are released from tumor cells during and after effective chemotherapy, with an initial peak in excretion and in serum levels and subsequent drop toward normal values; and (3) chemotherapy which produces only bone marrow (or other normal tissue) toxicity, and is without antitumor effectiveness, does not produce a significant increase in polyamine excretion. The latter observation would suggest either that cancer cells have much higher levels of polyamines than normal cells, even those with higher rates of DNA synthesis, or that therapy which is effective produces rather specific effects on polyamine synthesis in cancer cells. Thus, the depletion of spermidine is associated with the action of MGBG.

In studies conducted on men, toxicological effects observed clinically have been attributed to cumulative effects of repeated daily doses. This cumulation of accretion of toxicity is possibly explained by the unusually prolonged period required for urinary elimination of MGBG in man. Bioavailability studies in man with MGBG-$C^{14}$ have shown that following a single intravenous infusion over a period of 20 minutes, the radioactivity rapidly disappeared from the plasma and that over an extended period of 3 weeks approximately 60 percent of the drug was excreted unchanged in the urine. These data suggest that MGBG accumulates in the tissues and is slowly leached from tissue deposits to accomplish elimination.

The patentee, after considerably large number of studies conducted with MGBG in the treatment of various tumors, concludes that a weekly schedule of administration is most effective in achieving a higher therapeutic index while reducing toxicity to an acceptable level. Accordingly, a dose range of from 250 mg/$m^2$ to 1000 mg/$m^2$ of MGBG administered at weekly intervals was established for the treatment of various tumors.

While the above-indicated dose range decreases toxicological side effects and affords treatments of various tumors, long term accumulation of MGBG is still a problem requiring further studies and/or treatment modifications.

Applicants have conducted extensive studies of MGBG with the object to further reduce toxic side effects thereof. In the course of their studies it was discovered that MGBG contains relatively large amounts of impurities which may contribute to the toxicological side effects of MGBG. Accordingly, great efforts were expended to identify and reduce the amount of impurities present in MGBG and its salts.

SUMMARY OF THE INVENTION

We have now discovered a process for the synthesis and purification of MGBG dihydrochloride which provides a highly purified product with high yields. The product is useful in the treatment of cancer and other diseases including malignant diseases.

The process of the present invention comprises the steps of:

a) Removing 1,3-diaminoguanidine and other impurities from aminoguanidine bicarbonate by suspending aminoguanidine bicarbonate in water and filtering the suspension;

b) reacting the filtered aminoguanidine bicarbonate with methylglyoxal dimethyl acetal in a ratio of about 1 to 3 in a 2 to 3 mixture of water-isopropanol in a ratio of about 2 to 3 at a pH of from about 0 to 2, and preferably of from 0 to 1, at a temperature of from about 19° to about 40° C., and preferably of from about 28° to about 35° C., to produce the crystalline MGBG dihydrochloride salt; and c) purifying the crystalline MGBG dihydrochloride salt from a solution of acidic water-isopropanol medium.

DETAILED DESCRIPTION OF THE INVENTION

As used herein the process of synthesizing and purifying 2,2'-(1-methyl-1,2-ethanediylidene) bis[hydrazine carboximidamide] also relates to and includes synthesis and purification of its various forms including its hydrochloride monohydrate, dihydrate and hemihydrate forms.

The process of preparing guanylhydrazones is described by Baiocchi et al., *J. Med. Chem.*, 6, 431 (1963) and Oliverio, Denham, *J. Pharm. Sci.*, 52, 202 (1963).

The process comprises reacting an aminoguanidine salt with the corresponding carbonyl compound in an aqueous or aqueous-alcohol medium in the presence of a catalytic amount of acid.

The process uses commercially available aminoguanidine bicarbonate and is described as follows.

General Preparation of Guanylhydrazones

To a solution of 0.11 mole (15 g) of aminoguanidine bicarbonate in 125 mL of water was added slowly to the desired acid (a few drops of amyl alcohol was added in order to prevent foaming) until the pH of the solution was less than 7. The solution was filtered from trace amounts of insoluble solids. The appropriate carbonyl compound was then added to the slightly acid filtrate at ca 60° C. The amount of carbonyl compound used was such that the ratio of aminoguanidine per carbonyl function was 1:1. If the carbonyl compound did not dissolve in the aqueous mixture, ethanol was added until the reaction mixture was homogeneous. The solution was then stirred at room temperature for 16 hours. If a precipitate was formed the solid product was isolated by filtration. Otherwise the reaction mixture was evaporated until a solid residue was obtained using methanol, ethanol and a combination of solvents.

Recovery of guanylhydrazones was low.

In addition to low yield we have found that the products contained relatively large amounts of impurities.

This process was subsequently modified in order to obtain better yield and purer products.

The modified process of making MGBG dihydrochloride comprises the steps of:

a) reacting aminoguamidine bicarbonate with methyl glyoxal acetate to obtain the crude MGBG dihydrochloride;

b) purifying the crude product from a solution, precipitating and drying; and c) recrystallizing the purified product.

The details of the modified process are described in Example 1.

EXAMPLE 1

Guandine, 1,1'-(methyl]ethanediylidene)dinitrilo]di-, dihydrochloride, monohydrate (Methyl GAG), NSC-32,946

Aminoguanidine bicarbonate (5.0 kg, 36.7 mol) was dissolved in isopropanol (IPA; 1.56 L) and water (1.56 L) contained in a 50 L flask. Concentrated hydrochloric acid (3.14 L, 37.6 mol) was added to the solution (22°–30° C.) slowly over a 2.5 h period to avoid excessive foaming. The resulting solution was allowed to stand overnight with stirring. The next day, methylglyoxal dimethyl acetal (1.9 kg, 16 mol) was added slowly over 3 h with stirring (T=22°–27° C.). When the addition was complete, stirring was continued for 45 min. IPA (24.3 g, 19 L) was added and the mixture was stirred overnight. The next day the mixture was cooled to ca. 10° C. and filtered in two batches. The solid was washed with IPA (3×1 L) and low boiling petroleum either (3×1 L) and air dried for 40 h to give crude MGBG, 4.3 kg (48% based on the glyoxal). The above procedure was repeated to afford additional material (4.26 kg).

Purification, Removal of Trace Impurity

The above crude MGBG (8.55 kg) was dissolved in warm (45°–50° C.) deionized water (17.1 L) and cooled to ca. 35° C. Concentrated hydrochloric acid (48 mL) was added. Isopropanol (17 L) was added over 20 min. with stirring. The solution was cooled to 25° C. and held there for 1 h. The mixture was filtered through a one-inch celite pad to yield a clear straw-colored solution. Concentrated hydrochloric acid (191 mL) was added to the solution followed by the gradual addition, with vigorous stirring, of a mixture of ether (25.6 L) and IPA (34.2 L). Additional IPA (5.7 L) was added midway in the addition to avoid phase separation and IPA (5.7 L) was added to the remaining ether/IPA solution. The addition was completed in 2 h. The mixture was stirred vigorously another 30 min. and allowed to stand at ambient temperature overnight. The mixture was cooled to 15° C. and held there for 60 min. The precipitate was collected, washed with cold (~10° C.) IPA (3×3 L) and with a mixture of IPA and ether (2/1, v/v, 3×3 L) and air dried. A total of 9.16 kg of purified product was obtained. This material was vacuum dried for 48 hours at room temperature to afford 8.95 kg, 95% recovery.

Final Recrystallization

The above purified Methyl GAG (8.9 kg) was added in two portions (2×4.43 kg) to preheated (50°–60° C.) deionized water (2×4.4 L) with stirring. The solutions were filtered (filter paper) and combined to give a clear, straw-colored filtrate. Concentrated hydrochloric acid (13.4 mL) was added to the cooled (25° C.) solution with stirring. Then IPA (44.8 L) was added rapidly over 15 min. to the vigorously stirred solution. A total of 9.16 kg of purified product was obtained. This material was vacuum dried for 48 hours at room temperature to afford 8.95 kg, 95% recovery.

Although this modified process afforded improved yields, the product contained difficulty removable impurities. Accordingly, we have conducted studies to identify and to reduce/eliminate impurities from MGBG.

Experimental

We have developed methods for analysis of mitoguazone dihydrochloride using various systems to identify and quantify its impurities. One system of analysis included High Performance Liquid Chromatography. Considered in terms of determining chromatographic impurity levels, a high degree of specificity provides confidence that all the potential species of interest are detectable. Where these species, including process impurities and degradation products, are not available to inject directly onto the chromatographic system, specificity testing is usually conducted on stressed samples using one or more techniques which can usually be placed in one of two broad categories:

(a) Use of a specialized detection system to extract further information from the analyte peak.

(b) Some form of comparison between complimentary separation techniques, the first being the system under validation and the second being a system which, by virtue of its differing selectivity, might be expected to resolve species co-eluting in the first instance.

Examples of techniques in the first category include the use of diode array and mass spectroscopy detectors to obtain UV/Visible or mass spectra respectively from various positions through the analyte peak allowing, potentially, for the detection of co-eluting species. Techniques in the second category include the use of flow switching apparatus to divert the analyte peak onto a second stationary phase with a different selectivity, or comparison of results from the system being validated with those from a second chromatographic technique such as Thin Layer chromatography (TLC).

Equipment and Chemicals

HPLC data were generated using various Kontron (Watford, Herts) and Waters (Watford, Herts) pump, autosampler, column oven and detector models. HPLC data were processed using Multichrom™ V1.8–2 (LabSystems, Altringham, Cheshire). UV/visible absorption spectra were captured using an HP 1040 diode array detector (Hewlett Packard, Bracknell, Berks.). Light stressing (Xenon source, filtered through window glass) was performed in a Haraeus Suntest™ (Alplas Technology, Oxford). HPLC grade acetonitrile was obtained from Rathburn chemicals (Walkerburn, Scotland), HPLC grade heptane sulphonic acid (sodium slat), and inorganic chemicals were obtained from BDH limited (Poole, Dorset). ACVA (4,4'-Azobis(4-cyanovaleric acid), a radical initiator, exposure to which mimics oxidative stress, was obtained from Aldrich (Gillingham, Dorset). Mitoguazone dihydrochloride and purified water were obtained in-house.

Stress Sample Preparation

Samples of mitoguazone dihydrochloride (approximately 370 mg, equivalent to 250 mg base) were accurately weighed into 50 mL volumetric flasks and stressed according to the conditions given below. Stressing was continued for a maximum of 7 days or until 20 to 50% degradation had been achieved. After stressing, samples were neutralized, if necessary, and diluted to volume with purified water to give ~5 mg(base)/mL solutions for TLC analysis. Aliquots of these solutions were diluted with purified water to give ~1 mg(base)/mL solutions for use in impurity determinations by HPLC. Finally, aliquots of these solutions were either diluted in HPLC mobile phase to give ~0.01 mg(base)/mL solutions for HPLC assay.

Stress Conditions

Heat: Sample held at 80° C. for 7 days. Acidic: 10 mL of 0.1M hydrochloric acid was added to the sample and the solution held at 70° C. for 7 days. Basic: 10 mL of 0.1M sodium hydroxide was added to the sample and the solution held at 70° C. for 2 days. Aqueous: 10 mL of purified water was added to the sample and the solution held at 70° C. for 7 days. Oxidative: 10 mL of a 0.1M aqueous ACVA solution was added and the sample held at 40° C. for 7 days. Light: Sample received an overall illumination of ~15,000 klx hours (with associated UV). Assay: Samples were chromatographed isocratically on a 25 cm×0.46 i.d. Hypersil BDS C8 5 μm columns (Anachem, Luton, Beds.) using a mobile phase consisting of 0.05M potassium dihydrogen orthophosphate buffer containing 1 g/L of heptane sulphonic acid (sodium salt) and adjusted to pH 3.0 with concentrated orthophosphoric acid (89% by volume) and acetonitrile (11% by volume). The flow rate was 2 mL/minute, the detector wavelength was 283 nm, the injection volume was 20 μL and column temperature was 40° C. Samples were quantified with respect to an accurately prepared external standard (nominally 0.01 mg(base)/mL. Impurity Method: Chromatographic conditions were as for the assay except a detector wavelength of 210 nm was used. A second HPLC system was used with an aqueous to acetonitrile mobile phase ratio of 85% to 15% by volume, primarily to estimate specific process impurities. Impurities were quantified with respect to an accurately prepared external standard (nominally 0.005 mg(base)/mL).

TLC Method

20 μL of each sample was spotted onto a silica gel TLC plate (Merck 60 $F_{254}$). The plate was developed to a height of 10 cm in an acetone/ammonium hydroxide (SG 0.88)/water (90:5:5% by volume) mobile phase. Impurities were estimated against dilute mitoguazone dihydrochloride spots, both under short wavelength ultraviolet light (254 nm), and following treatment with a nitroprusside (sodium)-ferricyanide spray reagent.

Results

Triplicate samples representing 0, 80%, 100% and 120% of the nominal mitoguazone dihydrochloride concentration were analyzed. The results obtained are given in Table I.

TABLE I

Recovery Data

| Sample Identity | HPLC DATA* | |
|---|---|---|
| | % nominal added | % nominal recovered |
| Blank 1 | 0 | 0 |
| Blank 2 | 0 | 0 |
| Blank 3 | 0 | 0 |
| 80% 1 | 81.1 | 81.0 |
| 80% 2 | 80.9 | 80.4 |
| 80% 3 | 83.6 | 83.3 |
| 100% 1 | 101.5 | 101.6 |
| 100% 2 | 103.6 | 103.5 |
| 100% 3 | 104.6 | 104.2 |
| 120% 1 | 122.3 | 121.3 |
| 120% 2 | 121.9 | 122.5 |
| 120% 3 | 119.0 | 118.8 |

HPLC Assays*. Least Squares Regression Analysis of the data gave an average accuracy of 99.8% (Coefficient of Correlation 0.99935).

Analysis of Stressed Samples

Stressed samples were assayed by HPLC whilst chromatographic impurity levels were determined by HPLC and TLC. The chromatographic data are summarized in Table II.

TABLE II

Chromatographic Assay and Impurity Data for Stressed Mitoguazone Dihydrochloride

| Stress Condition | HPLC Assays (% w/w) | Impurities by HPLC (% w/w) | Impurities by TLC (% w/w) |
|---|---|---|---|
| Control | 100.6, 99.9 | 1.3 | <0.7 |
| Heat | 100.1, 100.2 | 1.1 | <1.1 |
| Acidic | 87.6, 87.0 | 14.0 | <12.5 |
| Basic | 74.9, 75.4 | 27.9 | <25.3 |
| Aqueous | 69.4, 69.1 | 31.9 | <29.5 |
| Oxidative | 93.7, 94.5 | 6.5 | <5.8 |
| Light | 99.9, 99.2 | 1.4 | <0.7 |

Using HPLC, TLC and mass spectroscopy, impurities contained in the starting materials or formed during the process of making the final product were identified and quantified.

We have found that diaminoguanidine related impurities account for more than 70% of the total MGBG-dihydrochloride impurity level.

The general reaction scheme for the production of the impurities and their chemical names follows.

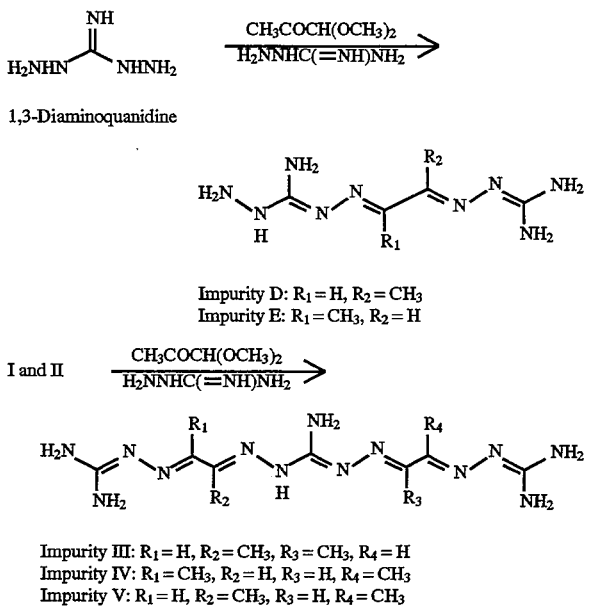

1,3-Diaminoguanidine

Impurity D: $R_1 = H$, $R_2 = CH_3$
Impurity E: $R_1 = CH_3$, $R_2 = H$

Impurity III: $R_1 = H$, $R_2 = CH_3$, $R_3 = CH_3$, $R_4 = H$
Impurity IV: $R_1 = CH_3$, $R_2 = H$, $R_3 = H$, $R_4 = CH_3$
Impurity V: $R_1 = H$, $R_2 = CH_3$, $R_3 = H$, $R_4 = CH_3$ wherein I=[2-[(Aminoiminomethyl)hydrazono]propylidene]-carbonimidic dihydrazide.

II=[2-[(Aminoiminomethyl)hydrazono]-1-methylethylidene]-carbonimidic dihydrazide.

III=Bis[2-[(Aminoiminomethyl)hydrazono]-1-methylethylidene]-carbonimidic dihydrazide.

IV=Bis[2-[(Aminoiminomethyl)hydrazono]propylidene]-carbonimidic dihydrazide.

V=[2-[(Aminoiminomethyl)hydrazono]-1-methylethylidene][2-[(aminoiminomethyl)hydrazono]propylidene]-carbonimidic dihydrazide.

In order to reduce the impurity levels in MGBG dihydrochloride, the process of Example 1 was modified based on further studies of the reaction parameters and recrystallization as discussed hereunder.

A. Reaction Parameters

1. Solvent and Solubility Properties of the Starting Materials

The solubility of aminoguanidine bicarbonate in most organic solvents is very limited and it has little or no solubility in water. The reaction medium in the procedure of Example 1 for the conversion of the bicarbonate salt to the hydrochloride is a 1:1 mixture of water to isopropanol. The slurry is converted to the hydrochloride salt by dropwise addition of concentrated HCl. The hydrochloride is very soluble in water. Therefore, no effort was made to change the choice of solvents (see Concentration).

Methylglyoxal dimethyl acetal is a light yellow oil with a b.p of 133°–135° C. It is soluble in most organic solvents and water.

Methylglyoxal Bis(guanylhydrazone) dihydrochloride is very soluble in water, DMSO, slightly soluble in methanol and insoluble in most other less polar solvents. It tenaciously holds onto one mole of water. In the reaction medium (aq. isopropanol) it crystallizes readily, but at the end of the reaction additional isopropanol is needed to achieve the overall yield of about 43% calculated on the basis of two moles of aminoguanidine bicarbonate.

2. Effect on pH

The pH of the medium is a critical parameter for the reaction of aminoguanidine with methylglyoxal dimethyl acetal. The end point of the procedure described in Example 1 had an end pH of about 4. The experiments listed in table III illustrate the effect of pH on yield. The second crop obtained was mainly unreacted aminoguanidine hydrochloride.

TABLE III

Synthesis of Mitoguazone (Crude)

| | | | | CROP | | CROP | |
|---|---|---|---|---|---|---|---|
| Code | Yield | Scale | pH* | 1st | Total Impur.*** | 2nd | Total Impur. |
| 163 | 30% | 500 g | 4–5 | 130 g | (2.92) | 116 g | ** |
| 173 | 82% | 500 g | 1–2 | 359 g | (1.01) | 28 g | (1.08) |
| 179 | 95% | 500 g | 0–1 | 420 g | (0.79) | — | — |
| 182 | 94% | 500 g | 0–1 | 415 g | (0.75) | — | — |
| 193 | 97% | 100 g | 0–1 | 93 g | (0.89) | — | — |
| 194 | 94% | 500 g | 0–1 | 460 g | (0.68) | — | — |
| 200 | 95% | 500 g | 0–1 | 464 g | (1.41) | — | — |

*pH taken after addition of HCl
**recovered aminoguanidine HCl - no product
***HPLC analysis 3. Concentration Experiments shown in Table III from 163 to 182 were carried out exactly as described in Example 1. The ratio of water to isopropanol was 1:1 and the concentration was 5 parts substrate to 3.12 parts solvent. This very concentrated mixture would not provide sufficient volume for effective stirring in a 50 gal reactor at the intended 20 kg scale. The ratio of water to isopropanol was adjusted to 2:3 and the volume was increased to provide a concentration of 5 parts substrate to 5 parts solvent. It is important to note the aminoguanidine HCl remains in solution without need of additional heating. The results obtained from this modification are shown in experiments 193 (100 g scale) and then 194 (500 g scale). Another variable was overlaid on these two experiments and is explained under Stoichiometry.

4. Rates of Addition and Timing of Operations

In Example 1, the addition of HCl to the aminoguanidine is carried out over 2.5 hours to avoid excessive foaming. On a 3.67 mole scale, the conversion could be completed in about 1.5 hours, but the ultimate rate should be dictated by the safe evolution of $CO_2$ gas from the reaction vessel.

The resulting solution was allowed to stand overnight according to the procedure. However, if a clear solution develops at 34° C. and if the pH is 0 to 1, there is no apparent reason to stir the reaction mixture overnight. In experiments 182, 193 and 194, the addition of the glyoxal was started within 1 hour after the HCl had been added.

The addition of methylglyoxal dimethylacetal was carried out over times that ranged from 1.5 hours to 3.5 hours as shown in Table IV. The rate of addition does not appear to be especially critical. The procedure calls for 2.5 hours, but some adjustment could be made for convenience of operation on kettle scale.

The precipitate resulting from the above operation was allowed to stir overnight. The next day, isopropanol was added to force more product out of solution. The mixture was cooled to 5°–10° C. for one hour and then filtered.

This sequence of operations is more streamlined and saves an additional day in the preparation of MGBG at no expense to purity or yield.

TABLE IV

| Code | Time of Addition | Temperature °C. |
|---|---|---|
| 163 | 3.5 hr | 25–29 |
| 173 | 3.0 hr | 27–28 |
| 179 | 2.5 hr | 27–29 |
| 182 | 2.0 hr | 28–40 |
| 193 | 1.5 hr | 30–31 |
| 194 | 1.5 hr | 30–35 |
| 200 | 2.5 hr | 25–30 |

5. Temperature

The conversion of the aminoguanidine bicarbonate salt to the HCl is an endothermic reaction. The temperature should be maintained at about 25°–30° C. by external warming.

The temperature ranges during the addition of methylglyoxal dimethylacetal are shown in Table IV. Some variability in temperature was purposely built into the experiments. However, there is no apparent advantage to carrying out the reaction at a slightly elevated temperature. The temperature range should be 28°–34° C.

6. Stoichiometry

The stoichiometry in experiments 173 through 182 was identical to the procedure of Table III. Methylglyoxal dimethylacetal (1.6 moles) reacts with 3.67 moles of aminoguanidine bicarbonate. However, on closer examination of the TLC of the crude product, low levels of unreacted aminoguanidine could be seen. Concentration of the ML's resulted in the isolation of about 10% unreacted aminoguanidine that was present in the stoichiometry of the process of Table III. Consequently, in experiments 193 and 194 the ratio was adjusted to 1.79:3.67 and the level of aminoguanidine appeared to diminish in both the crude product and the mother liquor. The yield was not seen to change significantly as a result of this change, however, it should be noted there was additional water in these experiments which could have a slightly negative impact on the recovery of MGBG.

Based on these observations, the stoichiometry should be a 1:2 ratio.

B. Recrystallization

1. Removal of Trace Impurity

The procedure of Example 1 incorporated a recrystallization from aq. isopropanol and diethyl ether subsequent to a filtration in order to remove a haze that was seen in solution of the final drug substance. One of our primary objects was to replace the potentially hazardous diethyl ether with a less volatile solvent that would achieve the same level of purification provided in the process of Example 1. The second objective was to identify the haze and develop methods to prevent its formation.

A series of recrystallization experiments was carried out on MGBG. The solvent chosen to replace diethyl ether was THF. In addition to being acceptable from a safety and environmental perspective, the water solubility of THF was advantageous in eliminating the biphasic separation seen with diethyl ether in the process of Example 1. Solvent volumes were scaled down to improve throughput and experiments were scaled up. The crystallization procedure is effective in achieving a purity level greater than that achieved in Example 1. A summary of the results is shown in Table V.

TABLE V

Recrystallization Experiments

| CODE | SCALE | SOLVENT ($H_2O$:IPROH: THF) | RATIO | ETI (HPLC BEFORE RECRYST.) | ETI (HPLC AFTER RE-CRYST) |
|---|---|---|---|---|---|
| Process* | 17 g | 34:125:51 | 16:60:24 | — | >1.50% |
| 174 | 17 g | 34:27:70 | 26:21:53 | 1.75 | 1.01% |
| 176 | 17 g | 30:23:60 | 27:20:53 | 1.75 | .94% |
| 181 | 85 g | 160:133:290 | 27:23:50 | 1.01 | .79% |
| 184 | 255 g | 480:400:870 | 27:23:50 | 1.01 | .93% |
| 185 | 383 g | 720:600:1305 | 27:23:50 | 0.75 | .85% |
| 188 | 383 g | 720:600:900 | 32:27:41 | 0.79 | .57% |

$H_2O$:IPROH:THF ratio - given in grams of solvent
*Example 1

2. Isolation of the Insoluble Impurity

Some crude batches of MGBG that were synthesized contained an insoluble haze in aqueous solutions. An aqueous isopropanol mixture was prepared from one of these batches according to the procedure of Example 1 and the insolubles were filtered to provide 1.8 g (0.5% of the total crude) of a white solid. The sample was refiltered from warm water to remove small amounts of MGBG. The impurity was presumed to be a polymer of pyruvaldehyde, but the C,H,N analysis was found to be very close to that of MGBG. The ms (LSIMS) gave an MH* 185 consistent for MGBG. Further evidence was seen in the electrospray ms for an MGBG sulfate or phosphate salt [MH+]283. The crude MGBG from experiment 173 was assayed by HPLC and found to be 99% pure. Subsequently, the insoluble material was assayed by HPLC and was also found to be consistent with MGBG. The exact identification of the salt was determined from the elemental analysis which indicated 10.8% sulfur. The most likely source of sulfate is from the starting aminoguanidine bicarbonate. A literature search revealed at least one manufacturing procedure which uses hydrazine sulfate in the reaction with cyanamide. The borate buffered product was neutralized with bicarbonate to provide the aminoguanidine bicarbonate. An analysis of aminoguanidine for sulfur has shown very low levels (0.025%).

The conclusion based on these findings is that removal of the sulfate salt will eliminate the haze problem.

3. Final Recrystallization

A final purification from one volume of deionized water at 50°–60° C. is described in Example 1. The solution was filtered, acidified and diluted further with isopropanol to provide the final product with a 94% recovery.

The recrystallization experiments are shown in Table VI. Experiment 160 followed the procedure of Example 1 which used a 1:5 ratio of water to isopropanol. In other experiments (160-195) the ratios were varied to determine the impact on recovery and purity. In experiments 195 and 196, the aqueous solution was diluted with a small volume of isopropanol before filtration. This was done to increase the solvent volume in order to allow efficient stirring in a 50 gal. reactor.

A modest improvement in purity was observed based on the recrystallization experiments shown in table VI.

TABLE VI

Final Recrystallization

| CODE | SOLVENT RATIO ($H_2O$:iPROH) | VOLUME | TOTAL IMP. (HPLC) CRUDE | TOTAL IMP. (HPLC) PURE | RECOVERY (%) |
|---|---|---|---|---|---|
| 160 | 18:82 | 6 | 1.22 | 1.13 | 93 |
| 191 | 60:40 | 1.7 | 1.13 | 0.99 | 87 |
| 192 | 24:76 | 8 | 1.13 | 1.03 | 87 |
| 195 | 30:70 | 6.8 | 1.03 | 0.73 | 86 |
| 196 | 30:70 | 6.8 | 0.89 | 0.77 | 83 |
| 197 | 30:70 | 6.8 | 0.68 | 0.65 | 91 |
| 001 | 30:70 | 6.7 | 1.94 | 1.61 | 82 |

Example 2 illustrates the process of the present invention incorporating the modifications found necessary based on the experimental findings described above.

EXAMPLE 2

EXPERIMENTAL

Step A 2,2'-(1-Methyl-1,2-ethanediylidene)bis[hydrazinecarboximidamide]

Aminoguanidine bicarbonate (Aldrich 98.5%) was slurried in DI water at 35°–40° C. for about 30 minutes, the suspension was filtered to remove diaminoguanidine and other impurities amounting to about 1% w/w. 505 g, 3.8 mol of the filtered aminoguanidine bicarbonate was suspended in 200 g DI water and 300 g (156 mL) isopropanol to give a heavy, but stirrable mixture. Concentrated HCl (376 g, 37.8%) was cautiously added dropwise over a 1.5 hr period to prevent excessive foaming (Note 1). The mixture stirred readily after 5% of the HCl had been added. The reaction was endothermic and the temperature was maintained at between 19° C. and 28° C. At the end of the addition a clear colorless solution was obtained (Note 2). It was warmed to 32° C. and stirred for 20 minutes (Note 3). The methyl glyoxal dimethylacetal (212 g, 1.79 mol) (Fluka, 98%) was next added over 1.5 hours at a temperature of 30°–35° ) (Note 4). The suspension was stirred overnight at ambient temperature. The next morning isopropanol (2.0 kg) was added over 15–20 minutes. The suspension was cooled to about 10° C. and stirring was continued for 1.5 hours. The solids were collected by filtration and rinsed with 2×200 mL isopropanol. After drying overnight in a vacuum oven at 30°–35° C., 463 g (47%) of the crude MGBG was obtained. TLC [acetone 90, water 5, $NH_4OH$ 5]; HPLC (ETI~0.79%); nmr (dmsod$_6$).

Note 1. The HCl must be added cautiously to prevent excessive build up of $CO_2$.

Note 2. Check pH and if necessary adjust pH to 0–1 by adding conc. HCl.

Note 3. In earlier experiments the mixture was allowed to stir overnight. This is unnecessary.

Note 4. In another experiment, the methylglyoxal dimethylacetal was added one hour after the addition of HCl with no apparent consequence. Stirring overnight is optional.

Note 5. About ⅔rds through the addition, the product begins to crystallize and a mild exotherm was observed.

Final Purification

A suspension of etude MGBG (460 g) in 920 g DI water was warmed to 40°–50° C. to give a clear pale yellow solution. The mixture was cooled to 30° C. and 920 mg conc. HCl was added. A pH of 0–1 was measured with litmus paper. Isopropanol (350 g, 446 mL) was added rapidly and the mixture stirred for 1 hour at 28°–32° C. The solutions were filtered to remove insoluble material. The filtrate was added to the reaction flask and acidified further with 0.5 g of conc. HCl The isopropanol (1.84 kg) was added over 10–15 minutes to the vigorously stirred solution. The mixture was cooled to 8°–12° C. and stirred for an additional hour. The solids were collected and the cake was rinsed with 2×200 mL isopropanol. After drying in a vacuum oven at 30°–40° C. for 24 hours, the recovery was about 90%. HPLC (ETI)=0.65%, nmr (dmsod$_6$); IR (Kbr).

The MGBG prepared according to the process of the present invention is at least 99.0% pure and is well-suited for the use in pharmaceutical compositions for the treatment of cancer and other diseases.

The invention has been described in detail with particular reference to certain preferred embodiments thereof, but it will be understood that variations and modifications can be effected within the spirit and scope of the invention.

What is claimed is:

1. A process for preparing 2,2'-(1-methyl-1,2-ethanediylidene)bis[hydrazine carboximidamide] comprising the steps of:

a) removing impurities from aminoguanidine bicarbonate by suspending aminoguanidine bicarbonate in water and filtering the suspension, said impurities having the formula

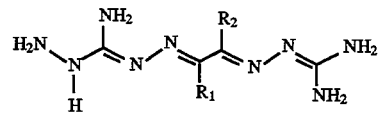

or

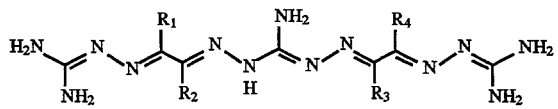

wherein $R_1$, $R_2$, $R_3$ and $R_4$ are independently H or $CH_3$;

b) reacting the filtered aminoguanidine bicarbonate with methylglyoxal dimethyl acetal in a ratio of about 1 to 3 in about a 2:3 reaction medium of water-isopropanol, at a pH of form about 0 to 2, and at a temperature of from about 19° to 20° C. to produce a crystalline 2,2'-1-methyl-1,2-ethanediylidene)bis[hydrazine carboximidamide]; and c) purifying the 2,2'-(1-methyl-1,2-ethanediylidene)bis[hydrazine carboximidamide] by recrystallization from an acidic aqueous-isopropanol medium.

2. The process of claim 1 wherein said reaction of aminoguanidine bicarbonate with methylglyoxal dimethyl acetal in water-isopropanol is at a pH of 0 to 1 and at a temperature of from 28° to 35° C.

3. The process of claim 1 wherein said purifying of the 2,2'-(1-methyl-1,2-ethanediylidene) bis[hydrazine carboximidamide] comprises the steps of:

(1) solubilizing the 2,2'-(1-methyl-1,2-ethanediylidene) bis[hydrazine carbox-imidamide] in water and acidifying it with hydrochloric acid;

(2) adding isopropanol to the solution and stirring the solution;

(3) filtering the solution to remove insoluble materials therefrom;

(4) further acidifying the filtered solution with hydrochloric acid followed by the addition of isopropyl alcohol to obtain the solid crystalline 2,2'-(1-methyl-1,2-ethanediylidine) bis[hydrazine carboximidamide]; and (5) filtering and drying the crystalline 2,2'-(1-methyl-1,2-ethanediylidine)bis [hydrazine carboximidamide].

4. 2,2'-(1-methyl-1,2-ethanediylidene)bis[hydrazine carboximidamide] prepared by the process of claim 1.

5. A method of treating cancer or malignant diseases in a mammal comprising: administering to said mammal an effective amount of a pharmaceutical composition containing the compound of claim 4.

* * * * *